(12) United States Patent
Kuban

(10) Patent No.: US 7,678,064 B2
(45) Date of Patent: Mar. 16, 2010

(54) APPARATUS FOR DETECTING TACTILE SENSITIVITY

(75) Inventor: Barry D. Kuban, Avon Lake, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 11/874,571

(22) Filed: Oct. 18, 2007

(65) Prior Publication Data
US 2008/0097236 A1 Apr. 24, 2008

Related U.S. Application Data

(60) Provisional application No. 60/853,355, filed on Oct. 20, 2006.

(51) Int. Cl.
A61B 19/00 (2006.01)
(52) U.S. Cl. ..................................................... 600/557
(58) Field of Classification Search ................. 600/552, 600/553, 557, 587, 594, 595; 606/237; 601/108, 601/101
See application file for complete search history.

(56) References Cited

U.S. PATENT DOCUMENTS

| 2,704,539 | A | * | 3/1955 | Fisher .......................... 600/557 |
| 3,662,744 | A | | 5/1972 | Low et al. |
| 3,933,148 | A | | 1/1976 | Wyler et al. |
| 4,313,446 | A | | 2/1982 | Kanatani |
| 4,467,815 | A | | 8/1984 | O'Brien et al. |
| 4,964,412 | A | * | 10/1990 | Kelly ........................... 600/553 |
| 5,195,532 | A | * | 3/1993 | Schumacher et al. ......... 600/552 |
| 5,316,011 | A | | 5/1994 | Weinstein et al. |
| 5,897,510 | A | * | 4/1999 | Keller et al. ................. 600/594 |
| 6,113,551 | A | | 9/2000 | Isaacs et al. |
| 6,234,976 | B1 | | 5/2001 | Linden |
| 6,234,977 | B1 | | 5/2001 | Christy |
| 6,306,101 | B1 | | 10/2001 | Vaynovsky et al. |

FOREIGN PATENT DOCUMENTS

WO WO 2004/045408 A1 6/2004

* cited by examiner

Primary Examiner—Brian Szmal
(74) Attorney, Agent, or Firm—Tarolli, Sundheim, Covell & Tummino LLP

(57) ABSTRACT

An apparatus for helping to determine tactile sensitivity of a patient includes a housing and a probe supported by the housing and having a probe tip. The probe is adapted for selective longitudinal movement relative to the housing between a first probe position, wherein the probe tip is substantially extended from the housing, and a second probe position, wherein the probe tip is substantially retracted into the housing. A first biasing means is adapted to urge the probe toward the first probe position. A predetermined motive force is selectively exerted between the probe tip and the patient to move the probe from the first probe position to the second probe position. The motive force is indicative of tactile sensitivity of the patient. A method for helping to determine tactile sensitivity of a patient is also described.

18 Claims, 3 Drawing Sheets

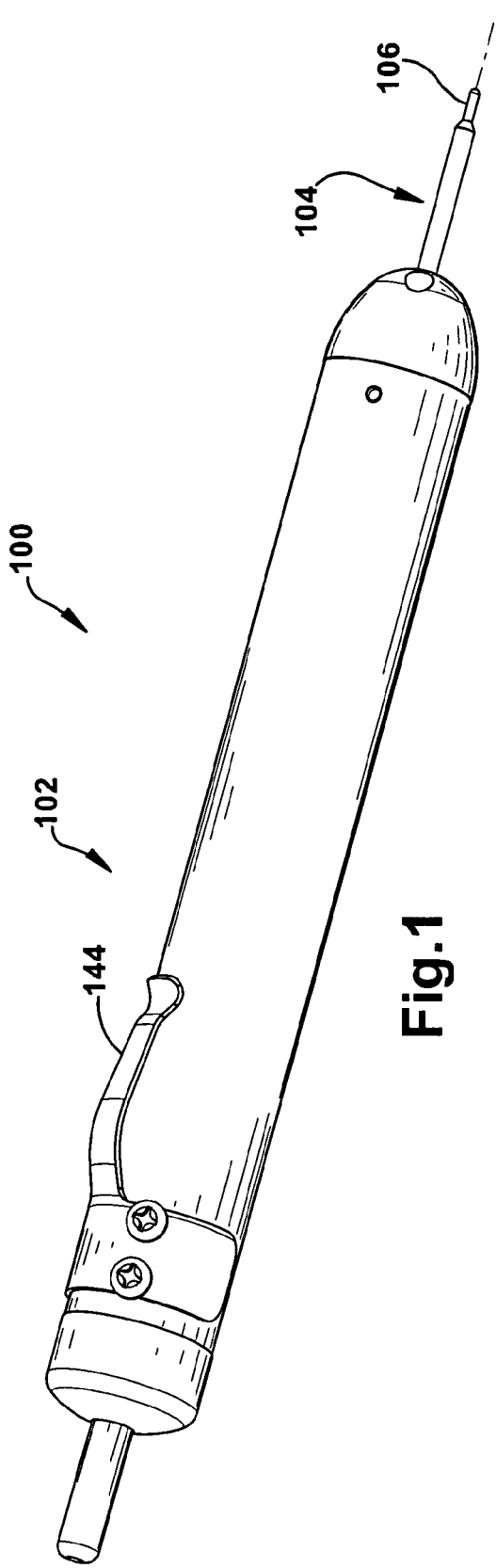
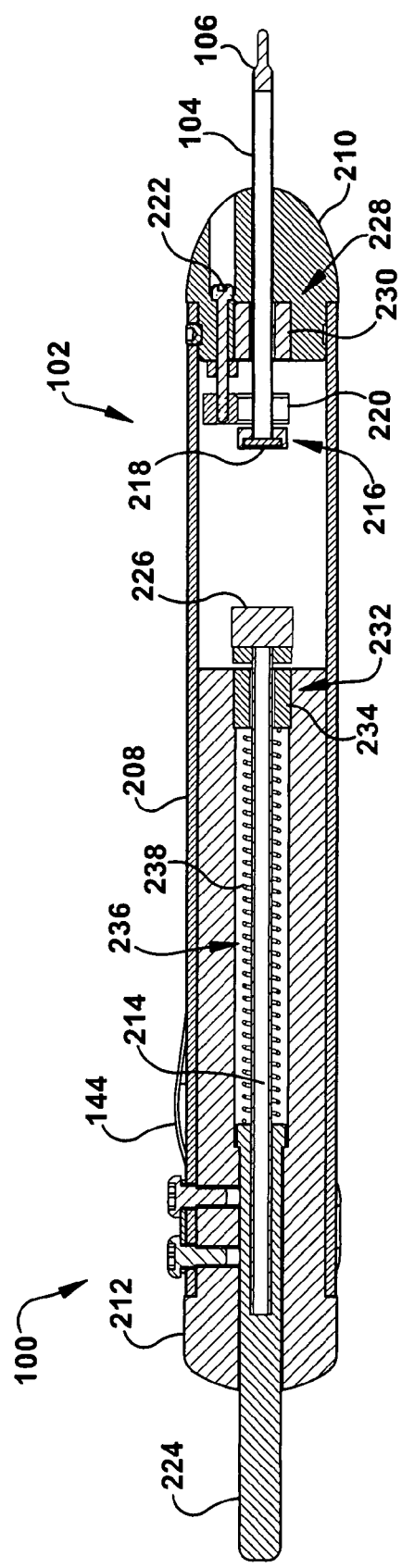

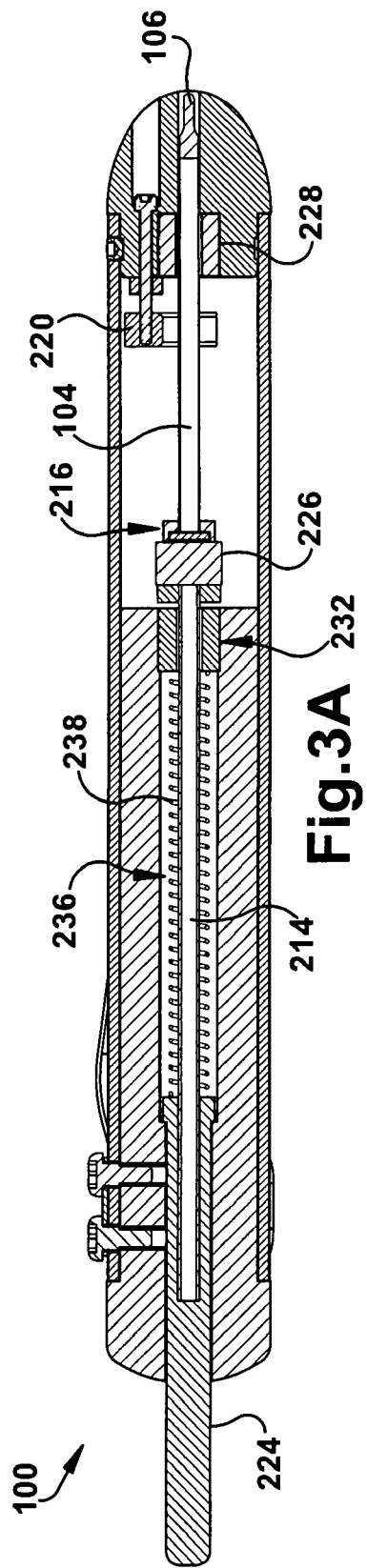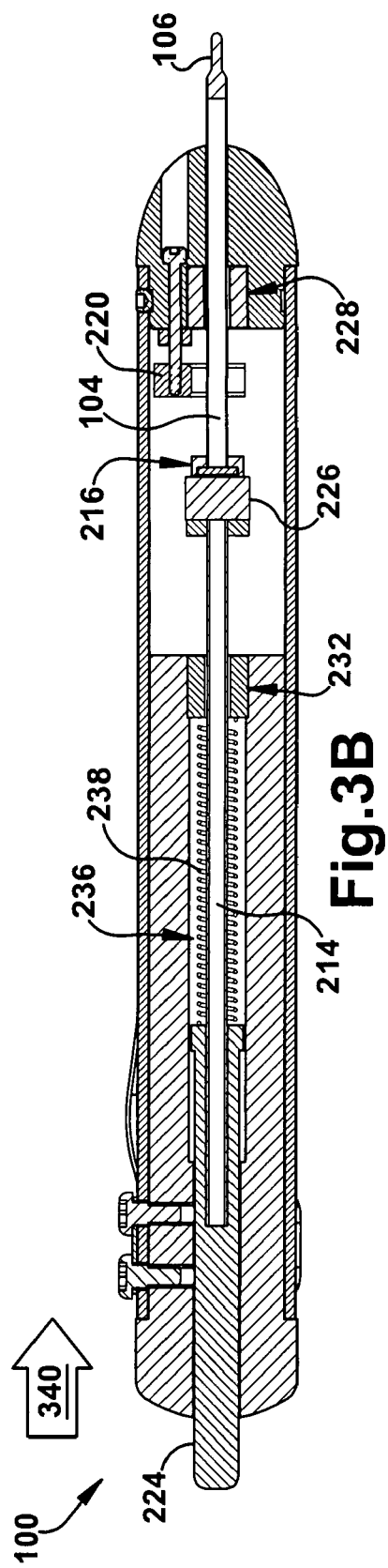

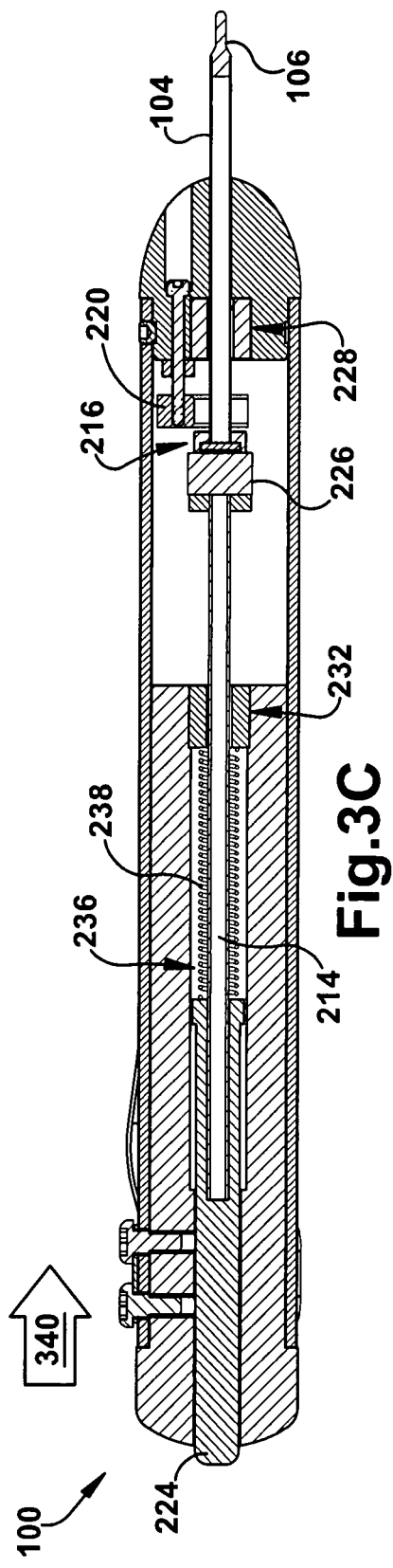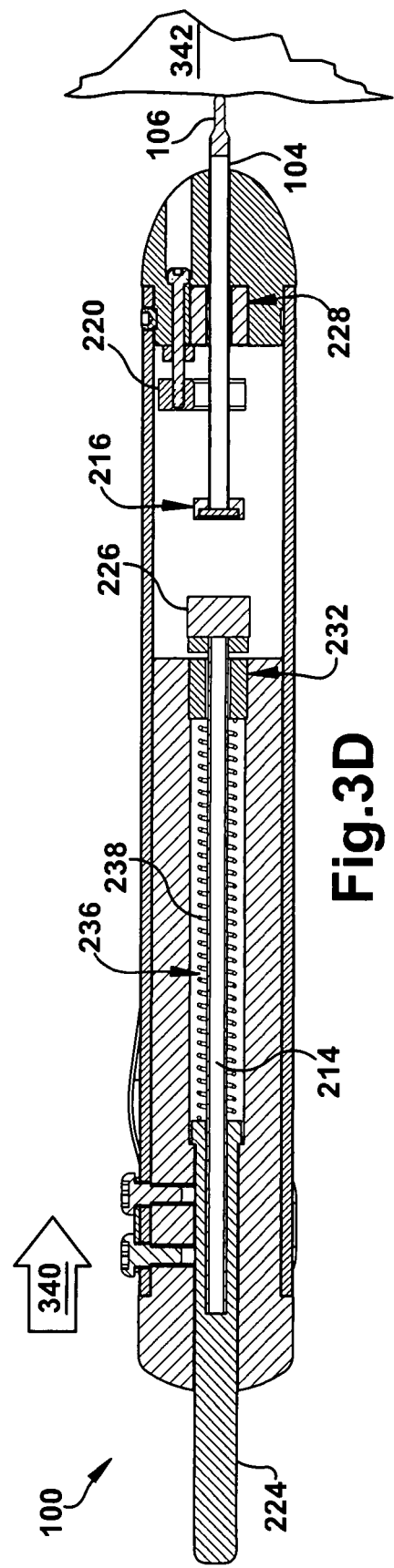

APPARATUS FOR DETECTING TACTILE SENSITIVITY

RELATED APPLICATION

This application claims priority from U.S. Provisional Application No. 60/853,355, filed Oct. 20, 2006, the subject matter of which is incorporated herein by reference.

TECHNICAL FIELD

The present invention relates to an apparatus for detecting tactile sensitivity. More particularly, the present invention relates to an apparatus for detecting the touch, pressure, or pain sensitivity of a patient.

BACKGROUND

There are a variety of circumstances in which it may be desired to measure, quantify, or otherwise determine the tactile sensitivity of a patient. For example, it may be desirable to determine pain thresholds experienced by a patient with a debilitating condition or illness. As another example, it may be desirable to determine a patient's ability to sense light force touches to the skin in order to help determine if the patient has lost sensation as a result of diabetes or other conditions which result in peripheral neuropathy. As a further example, it may be desirable to determine sensory neural deficits in patients with spinal cord injuries. Devices such as esthesiometers and algometers have been developed to measure these qualities.

SUMMARY OF THE INVENTION

In an embodiment of the present invention, an apparatus for helping to determine tactile sensitivity of a patient is described. The apparatus includes a housing and a probe supported by the housing and having a probe tip. The probe is adapted for selective longitudinal movement relative to the housing between a first probe position, wherein the probe tip is substantially extended from the housing, and a second probe position, wherein the probe tip is substantially retracted into the housing. A first biasing means is adapted to urge the probe toward the first probe position. A predetermined motive force is selectively exerted between the probe tip and the patient to move the probe from the first probe position to the second probe position. The motive force is indicative of tactile sensitivity of the patient.

In an embodiment of the present invention, a method for helping to determine tactile sensitivity of a patient is described. A testing apparatus having a probe adapted for selective longitudinal movement relative to a housing is provided. The probe is adapted for movement between a first probe position, wherein a probe tip is substantially extended from the housing, and a second probe position, wherein the probe tip is substantially retracted into the housing. The testing apparatus has a first biasing means being adapted to urge the probe toward the first probe position. The probe is placed in the first probe position. The patient is contacted with the probe tip. A predetermined motive force is exerted between the probe tip and the patient to move the probe from the first probe position to the second probe position. Tactile sensitivity of the patient is determined based on the motive force.

In an embodiment of the present invention, an apparatus for helping to determine tactile sensitivity of a patient is described. The apparatus includes a housing and a probe supported by the housing and having a probe tip. The probe is adapted for selective longitudinal movement relative to the housing between a first probe position, wherein the probe tip is substantially extended from the housing, and a second probe position, wherein the probe tip is substantially retracted into the housing. A first biasing means is adapted to urge the probe toward the first probe position. A second biasing means is adapted to urge the probe toward the second probe position. A calibration means has a calibration fork located inside the housing and a calibration screw operatively coupled to the calibration fork and accessible from outside the housing. The calibration screw is manipulable to change a distance between the first and second probe positions by changing a location of the calibration fork within the housing. A setting means includes a setting piston having a setting button located outside the housing and adapted for selective contact with a user, and a setting pad longitudinally spaced from the setting button, located inside the housing, and adapted for selective contact with the probe. The setting piston is selectively movable between a first setting position wherein the setting pad is located adjacent the first biasing means, and a second position wherein the setting pad is located adjacent the second biasing means. The setting means includes a piston biasing means adapted to bias the setting piston toward the second setting position. A predetermined motive force is selectively exerted between the probe tip and the patient to move the probe from the first probe position to the second probe position. The motive force is indicative of tactile sensitivity of the patient.

BRIEF DESCRIPTION OF THE DRAWINGS

For a better understanding of the invention, reference may be made to the accompanying drawings, in which:

FIG. 1 is a perspective view of one embodiment of the present invention;

FIG. 2 is a cross-sectional view of the embodiment of FIG. 1; and

FIGS. 3A, 3B, 3C, and 3D depict a sequence of operation of the embodiment of FIG. 1.

DESCRIPTION OF EMBODIMENTS

FIG. 1 depicts an apparatus 100 for detecting tactile sensitivity, such as touch, pressure, or pain sensitivity, of a patient by applying pressure to the patient's body and determining the lowest amount of pressure that the patient can feel and/or the highest amount of pressure that the patient can tolerate. The apparatus 100 may, for example, be used to help determine pain thresholds experienced by a patient with a debilitating condition or illness. Alternatively, the apparatus 100 may be used to help determine a patient's ability to sense light force touches to the skin in order to help determine if the patient has lost sensation as a result of diabetes or other conditions which result in peripheral neuropathy. As another alternative, the apparatus 100 may be used to help determine neural deficits in patients with spinal cord injuries. Indeed, the apparatus 100 may be used to detect tactile sensitivity related to any desired medical or physiological diagnosis or assessment.

As shown in FIG. 1, the apparatus 100 may be configured to have the general form factor of a pocket-sized implement, such as a pocket pen. The apparatus 100 is thus readily portable, such as in a shirt or jacket pocket, and can be manipulated easily by hand. The apparatus 100 has a longitudinally oriented housing 102 and a probe 104. The probe 104 is supported by the housing 102 and has a probe tip 106. The probe 104 is adapted for selective longitudinal movement relative to the housing 102 between a first probe position, in which the probe tip 106 is substantially extended from the housing as shown in FIG. 1, and a second probe position, wherein the probe tip is substantially retracted into the housing. A predetermined motive force is selectively exerted between the probe tip 106 and the patient (not shown) to move the probe 104 from the first probe position to the second probe position. The amount of motive force needed to move the probe 104 in this manner is indicative of tactile sensitivity of the patient. In other words, when testing loss of sensation of a patient and the amount of motive force is increased to a level detectable by the patient, that amount of motive force indicates the lowest end of the patient's ability to feel sensation at that location. Likewise, when testing a pain threshold of a patient and the amount of motive force is increased to a level which is uncomfortable to the patient, that amount of motive force indicates the highest end of the patient's ability to tolerate pain at that location. Thus, the patient's tactile sensitivity can be quantified using absolute numbers taken from the motive force needed to move the probe 104.

The cross-sectional view of FIG. 2 depicts the internal structure of the housing 102. A housing tube 208 may be made of aluminum or some other suitably rigid material. An end plug 210 is located at one end of the housing tube 208. The end plug 210 supports the probe 104 for longitudinal movement relative to the housing 102. A setting housing 212 is located at an end of the housing tube 208 opposite the end plug 210, and supports a setting piston 214 for longitudinal movement relative to the housing 102. In the illustrated embodiment, the housing 102 has a generally cylindrical configuration with a cylindrical housing tube 208. The housing 102 could, however, have any suitable alternative configuration, such as one having cylindrical portions as well as portions ergonomically contoured to facilitate handling the apparatus 100.

The probe 104 may include a probe cap 216 located longitudinally opposite the probe tip 106. The probe cap 216 remains inside the housing 102 during operation of the apparatus 100 and may include structure, such as a probe magnet 218, which interacts with other portions of the apparatus 100 as described below.

A calibration fork 220 is located inside the housing 102. A calibration screw 222 is operatively coupled to the calibration fork 220 and is accessible from outside the housing 102. The calibration screw 222 is manipulable to change a location of the calibration fork 220 within the housing 102 as desired by the user. By changing the location of the calibration fork 220 within the housing 102, the distance between the first and second probe positions may be changed, as will be discussed. Optionally, a calibration scale (not shown) may indicate to the user the location of the calibration fork 220 within the housing 102. The calibration fork 220, or another calibration means, is adapted to control a magnitude of the predetermined motive force to change an amount of tactile sensitivity indicated by the apparatus 100.

The setting piston 214 has a setting button 224 located outside the housing 102 and adapted for selective contact with a user. A setting pad 226 is located on the setting piston 214 longitudinally spaced from the setting button 224. The setting pad 226 is located inside the housing 102 and is adapted for selective contact with the probe 104. Optionally, the setting pad 226 is adapted for selective contact with the probe cap 216, as will be described in detail below with reference to FIGS. 3A, 3B, 3C, and 3D. The setting pad 226 may be made from as a soft and/or absorbent material, in order to dampen any sound that may occur when the probe 104 contacts the setting pad 226. Such sound might alert the patient to the fact that the probe 104 has moved, and therefore may affect the patient's ability to objectively indicate whether contact with the probe tip 106 was detected by the patient. The setting piston 214, or another setting means (not shown) is selectively manipulable to place the probe 104 into the first probe position, shown in FIG. 2.

The apparatus 100 also includes a first biasing means 228 adapted to urge the probe 104 toward the first probe position. As shown in FIG. 2, the first biasing means 228 may be a magnet 230 carried by the end plug 210. In the depicted embodiment, the probe cap 216 is magnetically responsive, through inclusion of a magnet and/or a magnetically sensitive metallic component, such as the probe magnet 218, in the probe cap 216. Therefore, the magnet 230 attracts the probe cap 216.

The probe cap 216 is permitted to approach the magnet 230 to the extent permitted by the position of the calibration fork 220, which is located between the probe cap 216 and the magnet 230. The magnetic force exerted by the magnet 230 on the probe cap 216 rises as the probe cap approaches the magnet and falls as the probe cap recedes from the magnet. Therefore, the calibration fork 220 may be moved by the calibration screw 222 to change the maximum magnetic force which can develop between the probe cap 216 and the magnet 230 by changing the first probe position with respect to the magnet 230.

For example, a maximum magnetic force occurring when the first probe position allows the probe cap 216 to approach fairly close to the magnet 230 is larger than a maximum magnetic force occurring when the first probe position is chosen to hold the probe cap 216 at a more distant position from the magnet 230. This maximum magnetic force is substantially the same as the predetermined motive force needed to move the probe 104 from the first probe position to the second probe position. Accordingly, a first probe position in which the probe cap 216 is closely proximate the magnet 230 will require a larger motive force (which indicates a lower tactile sensitivity or higher pain threshold of the patient) to move the probe 104 than will a first probe position in which the probe cap 216 is spaced further from the magnet 230.

The apparatus 100 may include a second biasing means 232 adapted to urge the probe 104 toward the second probe position. The second probe position is the position at which the probe tip 106 is substantially retracted into the housing 102 and is a storage or non-use position, as opposed to the first probe position, in which the apparatus 100 is ready for use to test tactile sensitivity of the patient. As shown in FIG. 2, the second biasing means 232 may be a magnet 234 carried by the setting housing 212 and adapted to act upon a magnetically sensitive probe cap 216.

FIG. 2 depicts the probe 104 in the first probe position and ready for use. Motive force may be exerted on the probe tip 106 from the right, in the FIG. 2 orientation. If the motive force is sufficient to overcome the magnetic attraction between the magnet 230 of the first biasing means 228 and the probe cap 216, the probe 104 starts to be pushed into the housing 102. When the probe 104 is pushed a sufficient distance into the housing 102, the probe cap 216 begins to be attracted to the magnet 234 of the second biasing means 232. The probe 104 is then rapidly retracted into the housing 102 under the magnetic force between the probe cap 216 and the magnet 234, and is held in the second probe position as discussed below, until the user takes some positive action to release the probe 104 from the second probe position.

An example of a setting means that can be used to release the probe 104 from the second probe position is the setting piston 214 and related structure shown in FIG. 2. The setting piston is selectively moveable between a first setting position and a second setting position, with the setting piston 214 shown in the second setting position in FIG. 2. In the second setting position, the setting pad 226 of the setting piston 214 is located adjacent the second biasing means 232. "Adjacent" is used herein to mean "nearby", in contrast to a widely spaced relationship. Two "adjacent" members may have other intervening structures located at least partially in between, but all of the adjacent members and the intervening structures are clustered together in close proximity. The adjacent members need not touch each other or be touching the same intervening structure.

A piston biasing means 236, such as the spring 238 shown in the Figures, is adapted to bias the setting piston 214 toward the second setting position. However, a setting force could be exerted by the user on the setting button 224 to overcome the piston biasing means 236 and thereby move the setting piston 214 into the first setting position. In the first setting position, the setting pad 226 is located adjacent the first biasing means 228.

The sequence of FIGS. 3A, 3B, 3C, and 3D illustrates the movement of the probe 104 between the second and first probe positions, and the setting piston 214 between the second and first setting positions. In FIG. 3A, the apparatus 100 is in a storage mode, with the probe 104 in the second probe position and the setting piston 214 in the second setting position. The piston biasing means 236 is holding the setting piston 214 in the second setting position. The second biasing means 232 is holding the probe 104 in the second probe position, with the setting pad 226 located between the probe cap 216 and the second biasing means 232, with all three of these structures being located adjacent each other. The apparatus 100 may be readily carried or stored by the user when in the FIG. 3A configuration.

When the user is ready to use the apparatus, a positive action is taken to place the probe 103 into the first probe position. As shown in FIG. 3B, a motive force is exerted by the user on the setting button 224 in the direction of arrow 340. This motive force is sufficient to overcome the piston biasing means 236 and the setting piston 214 begins to move in the direction of arrow 340. As the setting piston 214 moves away from the second setting position, the probe 104 is pushed away from the second biasing means 232 and thus away from the second probe position. FIG. 3B depicts an intermediate setting mode of the apparatus 100, wherein both the probe 104 and the setting piston 214 are in between their first and second probe positions and first and second setting positions, respectively.

In FIG. 3C, the motive force exerted by the user on the setting button 224 in the direction of arrow 340 has moved the setting piston 214 to push the probe 104 into the first probe position. The setting piston 214 is shown in the first setting position in FIG. 3C. The probe cap 216 is prevented from further travel in the direction of arrow 340 toward the first biasing means 228 by the calibration fork 220. The probe cap 216 is located between the setting pad 226 and the first biasing means 228, with all three of these structures being located adjacent each other. The apparatus 100 will remain in the configuration of FIG. 3C as long as sufficient force is exerted on the setting button 224 to overcome the biasing force exerted on the setting piston 214 by the piston biasing means 236.

When the apparatus 100 is in the configuration of FIG. 3C and the user releases the setting button 224, the piston biasing means 236 causes the setting piston 214 to return to the second setting position. However, the first biasing means 228 exerts force on the probe 104 sufficient to retain the probe 104 in the first probe position despite the movement of the setting piston 214. Therefore, the apparatus 100 will attain the ready mode configuration shown in FIG. 2 upon release of the setting piston 214 from the first setting position to the second setting position.

From the ready mode of FIG. 2, the user may contact a body portion 342 of the patient with the probe tip 106. A motive force in the orientation of arrow 340 is exerted between the probe tip 106 and the body portion 342. Once the motive force has reached a predetermined level, the first biasing means 228 is overcome and the probe 104 may begin to move from the first probe position to the second probe position, as shown in the intermediate use mode configuration of FIG. 3D.

When the probe 104 returns to the second probe position, the apparatus 100 re-attains the storage mode configuration shown in FIG. 3A. The amount of pressure against the probe tip 106 needed to develop the predetermined level of motive force to move the probe away from the first biasing means 228 can then be correlated with the tactile sensitivity of the patient. This calibration is achieved by calibrating the apparatus 100, as described below, to control a magnitude of the predetermined motive force to change an amount of tactile sensitivity indicated by the apparatus, as needed.

For example, if the patient is being tested for loss of sensation of a certain skin area, the apparatus 100 could be calibrated, via the calibration screw 222 or another calibration means (not shown), to require a relatively low predetermined level of motive force to move the probe away from the first biasing means 228. It may be desirable to carry out the testing with the patient prevented from seeing at least a portion of the apparatus 100, so that the patient's indication of tactile sensation is not influenced by visual detection of movement of the probe 104. If the patient cannot feel pressure from the probe tip 106 as the motive force is exerted, the apparatus 100 could be recalibrated to require a higher predetermined level of motive force to move the probe away from the first biasing means 228. The setting button 224 may then be utilized as described above to once again change the apparatus 100 from the storage mode of FIG. 3A to the use mode of FIG. 2, and the testing process outlined above may be repeated. If the patient still cannot feel pressure from the probe tip 106 as the motive force is exerted, the apparatus 100 could be recalibrated to require an even higher predetermined level of motive force to move the probe away from the first biasing means 228. This testing and recalibrating, increasing-pressure cycle may be repeated until the patient can feel pressure from the probe tip 106, at which point the patient's lowest tactile sensitivity is established. The increasing-pressure cycle may also or instead be used to test the pain tolerance of a patient. The pressure needed to develop the predetermined level of motive force may be increased with each round of testing until the patient indicates that the pressure is too high for comfort.

When a second biasing means 232 is present, as shown in the Figures, the second biasing means acts to hold the probe 104 in the second probe position until released by action of the setting piston 214. The second biasing means 232 also may act to help retract the probe 104 from the first probe position, shown in FIG. 2, to the second probe position, shown in FIG. 3A. The second biasing means 232, whether a magnet, spring, or other biasing structure, should exert sufficient biasing force on the probe 104 to perform these functions. However, the strength of the second biasing means 232 should be chosen so as not to assist the predetermined motive force in overcoming the first biasing means 228 and thereby skew the results of testing with the apparatus 100.

A pocket clip 144, as shown in FIG. 1, may be provided and attached to the housing 102 or another structure of the apparatus 100, to facilitate availability of the apparatus 100 to the user in a clinical setting. A cover or sheath (not shown) may also be provided to cover a portion of the apparatus 100 and protect that portion from inadvertent actuation or debris entry. For example, and particularly when no second biasing means 232 is provided, an end cap (much like a pen cap) may be provided to keep the probe tip 106 from spontaneously extending from the housing 102 and being bent or broken.

It is also contemplated that a small screwdriver (not shown) may be supplied as an accessory to the apparatus 100, so that the user does not have to separately supply a screwdriver each time the calibration screw 222 needs to be adjusted. Since this screwdriver will likely be rather small and prone to loss, a portion of the apparatus 100, such as the setting housing 212, could include a cavity (not shown) or another structure adapted to securely but removably hold the screwdriver ready for use as needed. Alternatively, the screwdriver could be permanently attached to, or integrally formed with, the calibration screw 222 so that the user can readily adjust the position of the calibration fork 220 as needed.

The first and second biasing means 228 and 232 are discussed above as including magnets 230 and 234, respectively, with the probe cap 216 being magnetically responsive. The first and/or second biasing means 228 and 232 could also or instead use a spring (not shown) or other biasing member to urge the probe 104 into the respective first and second probe positions. Likewise, the piston biasing means 236 is discussed above as being a spring, but could also or instead be a magnet or other biasing member to bias the setting piston 214 toward the second setting position. Depending upon the design of the first and/or second biasing means 228 and 232 or the piston biasing means 236, they may be located in a different area of the housing 102 than shown. For example, if the first biasing means 228 is a tension spring, a different location will be required to achieve the desired biasing results than if the first biasing means is a compression spring.

Magnetic biasing may be more desirable than other biasing means for use in certain applications of the apparatus 100 because of the force response of a magnetic means. Namely, the peak force that is applied by a magnetic first and/or second biasing means 228 and 232 occurs at the moment the probe 104 begins to move, and the applied force at any other point during travel of the probe between the first and second probe positions is necessarily lower. Therefore, the peak applied force may be independent of the location of the probe 104 within the housing 102. Because of this "humped" force response, an apparatus 100 using magnetic biasing means is not susceptible to inaccuracies caused by a "force overshoot" that could result from movement of the probe 104 past the target position in a monotonic biasing mechanism, such as a spring. However, one of ordinary skill in the art could readily take this force response into account when choosing any of the first and/or second biasing means 228 and 232 or the piston biasing means 236 for the apparatus 100, and a magnetic biasing means is not necessarily preferred for all applications of the apparatus.

The magnets discussed herein could be of any suitable type, such as magnetized metal or polymer, rare earth type magnets, or the like, but should be permanent magnets (i.e., not subject to demagnetization over time). The springs discussed herein could be of any suitable type, such as coil, leaf, flat, or any other type, and may be used in tension or compression. To help maintain the consistency or uniformity of the biasing force exerted by the first and/or second biasing means 228 and 232 or the piston biasing means 236, especially when a spring is used for such, the apparatus 100 may include guides (not shown) for permitting axial movement (e.g., compression or extension) of the spring while preventing or limiting lateral movement (e.g., bending or deflection) of the spring. Any of the biasing means 228, 232, and 236 discussed herein could also or instead include a pneumatic mechanism, such as a piston-cylinder arrangement, configured to utilize a compressed gas to provide a biasing force. A suitable biasing means 228, 232, or 236 can readily be designed by one of ordinary skill in the art.

While operating the apparatus 100, care should be exercised to apply mainly longitudinal loads to the probe 104 while avoiding applying loads to the probe in other, non-longitudinal directions. The apparatus 100 should be constructed and arranged to help minimize the effects of non-axial loads on the probe 104 as well as to optimize other factors that can affect the operation or accuracy of the apparatus. The probe 104 and other structures of the apparatus 100 may be molded, machined, or otherwise formed with a high precision, close tolerance fit using low friction materials with smooth surfaces to help minimize the effects of friction. The probe 104 also may be constructed of a lightweight plastic material to help minimize the effects of gravity when using the apparatus 100 in different orientations.

While aspects of the present invention have been particularly shown and described with reference to the preferred embodiment above, it will be understood by those of ordinary skill in the art that various additional embodiments may be contemplated without departing from the spirit and scope of the present invention. For example, any structure of the apparatus 100 could be made at least partially from a low-friction material such as Teflon®, or from any other suitable material or combination of materials as chosen by one of ordinary skill in the art. Though the structures of the apparatus 100 are depicted as moving and acting on each other in a linear longitudinal direction or orientation, there could be at least some aspects of the motion or interaction of structures which differ from that orientation. Forces described or depicted as being substantially equivalent could differ by a small degree due to frictional losses or other minor discrepancies. The structures of the apparatus 100 could be formed as any number of suitable subassemblies and could be attached together by molding, adhesives, interference/frictional fits, fasteners, or any other suitable means. The calibration fork 220 could be moved within the housing 102 by a mechanism other than, or in addition to, the calibration screw 222. The setting pad 226 could be selectively magnetizable, to attract or repel the probe cap 216 as desired during different stages of operation of the apparatus 100. Normally the patient will stay stationary while the apparatus 100 is moved to exert the predetermined motive force, but the patient may instead move against a stationary apparatus 100. There may be, but need not be, a relationship between the motive force needed to move the probe 104 from the first probe position to the second probe position and the motive force needed to move the probe 104 from the second probe position to the first probe position. A plurality of apparatuses 100 could be provided, with each apparatus 100 having a different predetermined motive force needed to move the probe 104, to prevent the user from having to recalibrate the apparatus 100. Different sizes of apparatuses 100 may be provided, with each size being adapted to require a different amount or range of predetermined motive forces. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, I claim:

1. An apparatus for helping to determine tactile sensitivity of a patient, the apparatus comprising:
   a housing;
   a probe supported by the housing and having a probe tip and an elongate probe body, the probe body longitudinally extending between a probe cap and the probe tip, the probe being adapted for selective longitudinal movement relative to the housing between a first probe position, wherein the probe tip and the probe body are substantially extended from the housing, and a second probe position, wherein the probe tip is substantially retracted into the housing and the probe body is retracted into the housing;
   a first biasing means adapted to urge the probe toward the first probe position; and
   a second biasing means adapted to urge the probe toward the second probe position;
   wherein a predetermined motive force is selectively exerted between the probe tip and the patient to move the probe from the first probe position to the second probe position, and the motive force is indicative of tactile sensitivity of the patient;
   wherein at least one of the first and second biasing means includes a magnet, the probe cap being located longitudinally between the first and second biasing means and being magnetically responsive.

2. The apparatus of claim 1, wherein at least one of the first and second biasing means includes a spring.

3. The apparatus of claim 1, including a calibration means, wherein the calibration means is adapted to control a magnitude of the predetermined motive force to change an amount of tactile sensitivity indicated by the apparatus.

4. The apparatus of claim 3, wherein the calibration means includes a calibration fork located inside the housing and a calibration screw operatively coupled to the calibration fork and accessible from outside the housing, the calibration screw being manipulable to change a distance between the first and second probe positions by changing a location of the calibration fork within the housing.

5. The apparatus of claim 1, including a setting means, wherein the setting means is selectively manipulable to place the probe in the first probe position.

6. The apparatus of claim 5, wherein the setting means includes a setting piston having a setting button located outside the housing and adapted for selective contact with a user, and a setting pad longitudinally spaced from the setting button, located inside the housing, and adapted for selective contact with the probe, the setting piston being selectively movable between a first setting position wherein the setting pad is located adjacent the first biasing means, and a second position wherein the setting pad is located adjacent the second biasing means, the setting means including a piston biasing means adapted to bias the setting piston toward the second setting position.

7. The apparatus of claim 6, wherein the piston biasing means is a spring.

8. A method for helping to determine tactile sensitivity of a patient, the method comprising the steps of:
   providing a testing apparatus having a probe supported by a housing and having a probe tip and elongate probe body, the probe body longitudinally extending between a probe cap and the probe tip, the probe being adapted for selective longitudinal movement relative to the housing between a first probe position, wherein the probe tip and the probe body are substantially extended from the housing, and a second probe position, wherein the probe tip is substantially retracted into the housing and the probe body is retracted into the housing, the testing apparatus having a first biasing means adapted to urge the probe toward the first probe position;
   placing the probe in the first probe position;
   contacting the patient with the probe tip;
   exerting a predetermined motive force between the probe tip and the patient to move the probe from the first probe position to the second probe position; and
   determining tactile sensitivity of the patient based on the motive force;
   wherein the testing apparatus includes a second biasing means being adapted to urge the probe toward the second probe position;
   wherein at least one of the first and second biasing means includes a magnet and the probe is magnetically responsive, and the step of exerting a predetermined motive force between the probe tip and the patient to move the probe from the first probe position to the second probe position includes the step of overcoming the magnetic force of the first biasing means to move the probe away from the first probe position.

9. The method of claim 8, wherein at least one of the first and second biasing means includes a spring, and the step of exerting a predetermined motive force between the probe tip and the patient to move the probe from the first probe position to the second probe position includes the step of overcoming the spring force of the first biasing means to move the probe away from the first probe position.

10. The method of claim 8, including the step of calibrating the apparatus by controlling a magnitude of the predetermined motive force to change an amount of tactile sensitivity indicated by the apparatus.

11. The method of claim 10, wherein the step of calibrating the apparatus includes the steps of:
   providing a calibration fork located inside the housing and a calibration screw operatively coupled to the calibration fork and accessible from outside the housing; and
   manipulating the calibration screw to change a distance between the first and second probe positions by changing a location of the calibration fork within the housing.

12. The method of claim 8, wherein the step of placing the probe in the first probe position includes the step of selectively manipulating a setting means to place the probe in the first probe position.

13. The method of claim 12, wherein the setting means includes a setting piston having a setting button located outside the housing and adapted for selective contact with a user, and a setting pad longitudinally spaced from the setting button, located inside the housing, and adapted for selective contact with the probe, the setting piston being selectively movable between a first setting position wherein the setting pad is located adjacent the first biasing means, and a second position wherein the setting pad is located adjacent the second biasing means, the setting means including a piston biasing means adapted to bias the setting piston toward the second setting position, and the step of selectively manipulating a setting means to place the probe in the first probe position includes the step of overcoming the piston biasing means by manipulating the setting button.

14. The method of claim 13, wherein the piston biasing means is a spring.

15. An apparatus for helping to determine tactile sensitivity of a patient, the apparatus comprising:

a housing;

a probe supported by the housing and having a probe tip, the probe being adapted for selective longitudinal movement relative to the housing between a first probe position, wherein the probe tip is substantially extended from the housing, and a second probe position, wherein the probe tip is substantially retracted into the housing;

a first biasing means being adapted to urge the probe toward the first probe position;

a second biasing means being adapted to urge the probe toward the second probe position;

a calibration means having a calibration fork located inside the housing and a calibration screw operatively coupled to the calibration fork and accessible from outside the housing, the calibration screw being manipulable to change a distance between the first and second probe positions by changing a location of the calibration fork within the housing; and a setting means having a setting piston having a setting button located outside the housing and adapted for selective contact with a user, and a setting pad longitudinally spaced from the setting button, located inside the housing, and adapted for selective contact with the probe, the setting piston being selectively movable between a first setting position wherein the setting pad is located adjacent the first biasing means, and a second position wherein the setting pad is located adjacent the second biasing means, the setting means including a piston biasing means adapted to bias the setting piston toward the second setting position;

wherein a predetermined motive force is selectively exerted between the probe tip and the patient to move the probe from the first probe position to the second probe position, and the motive force is indicative of tactile sensitivity of the patient.

16. The apparatus of claim 15, wherein at least one of the first and second biasing means includes a magnet and the probe includes a probe cap longitudinally spaced from the probe tip, the probe cap being located longitudinally between the first and second biasing means and being magnetically responsive.

17. The apparatus of claim 15, wherein at least one of the first and second biasing means includes a spring.

18. The apparatus of claim 15, wherein the piston biasing means is a spring.

* * * * *